United States Patent
Murayama

(10) Patent No.: US 11,209,532 B2
(45) Date of Patent: Dec. 28, 2021

(54) SIGNAL PROCESSING DEVICE, PHOTOACOUSTIC WAVE IMAGE-ACQUISITION DEVICE, AND SIGNAL PROCESSING METHOD

(71) Applicant: OLYMPUS CORPORATION, Hachioji (JP)

(72) Inventor: Yoshiaki Murayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 340 days.

(21) Appl. No.: 16/517,627

(22) Filed: Jul. 21, 2019

(65) Prior Publication Data

US 2019/0339372 A1 Nov. 7, 2019

Related U.S. Application Data

(63) Continuation of application No. PCT/JP2017/002151, filed on Jan. 23, 2017.

(51) Int. Cl.
*G01S 7/52* (2006.01)
*G01S 15/89* (2006.01)

(52) U.S. Cl.
CPC ...... *G01S 7/52085* (2013.01); *G01S 7/52028* (2013.01); *G01S 7/52053* (2013.01); *G01S 15/8906* (2013.01)

(58) Field of Classification Search
CPC ............. G01S 7/52085; G01S 7/52028; G01S 7/52053; G01S 15/8906; A61B 5/0095; A61B 8/13
See application file for complete search history.

(56) References Cited

U.S. PATENT DOCUMENTS 10,309,933 B2 * 6/2019 Murayama ......... G01N 29/4427
2009/0323094 A1 * 12/2009 Hayashi ............... B41J 11/0095
358/1.12

(Continued)

FOREIGN PATENT DOCUMENTS

CN  105848587 A * 8/2016 ......... G01N 29/2418
EP   2138314 A1 * 12/2009 ............. B41J 11/42

(Continued)

OTHER PUBLICATIONS

International Search Report (ISR) dated Apr. 18, 2017 (and partial English translation thereof) issued in International Application No. PCT/JP2017/002151.

(Continued)

*Primary Examiner* — Daniel Pihulic
(74) *Attorney, Agent, or Firm* — Holtz, Holtz & Volek PC

(57) ABSTRACT

A signal processing device according to the present invention is a signal processing device that processes data of a detected ultrasound waveform representing a temporal change in the intensity of ultrasound generated at a measurement position in a specimen and includes: a comparison unit that compares a predetermined standard ultrasound waveform and the detected ultrasound waveform at the measurement position and that calculates a degree of similarity between the predetermined standard ultrasound waveform and the detected ultrasound waveform; and a discrimination unit for discriminating whether or not the measurement position corresponds to a predetermined examination subject on the basis of the degree of similarity.

10 Claims, 8 Drawing Sheets

(56) References Cited

U.S. PATENT DOCUMENTS

| | | |
|---|---|---|
| 2010/0268042 A1 | 10/2010 | Wang et al. |
| 2011/0201914 A1 | 8/2011 | Wang et al. |
| 2013/0245406 A1 | 9/2013 | Wang et al. |
| 2014/0142404 A1 | 5/2014 | Wang et al. |
| 2016/0081558 A1 | 3/2016 | Wang et al. |
| 2016/0249812 A1 | 9/2016 | Wang et al. |
| 2016/0305912 A1* | 10/2016 | Murayama ......... G01N 29/0681 |
| 2017/0196461 A1 | 7/2017 | Fukutani |
| 2019/0339372 A1* | 11/2019 | Murayama ......... G01S 7/52085 |

FOREIGN PATENT DOCUMENTS

| | | | | |
|---|---|---|---|---|
| JP | 2011519281 A | | 7/2011 | |
| JP | 2012075464 A | | 4/2012 | |
| JP | 2015123098 A | * | 7/2015 | ......... G01N 29/4427 |
| JP | 2015123098 A | | 7/2015 | |
| JP | 5850633 B2 | | 2/2016 | |
| KR | 20100002215 A | * | 1/2010 | ......... B41J 11/0095 |
| WO | 2009055705 A2 | | 4/2009 | |
| WO | 2012140865 A1 | | 10/2012 | |
| WO | 2015098018 A1 | | 7/2015 | |
| WO | WO-2015098018 A1 | * | 7/2015 | ............. G01N 29/44 |
| WO | WO-2018135005 A1 | * | 7/2018 | ......... G01S 7/52085 |

OTHER PUBLICATIONS

Yamamoto, et al., "Selective detection of photoacoustic signal using cross correlation method for photoacoustic imaging", Lecture I408pVII02, Pre-print for the Laser Society of Japan academic lecture annual meeting heal Jan. 7-9, 2017 at Tokushima University.

* cited by examiner

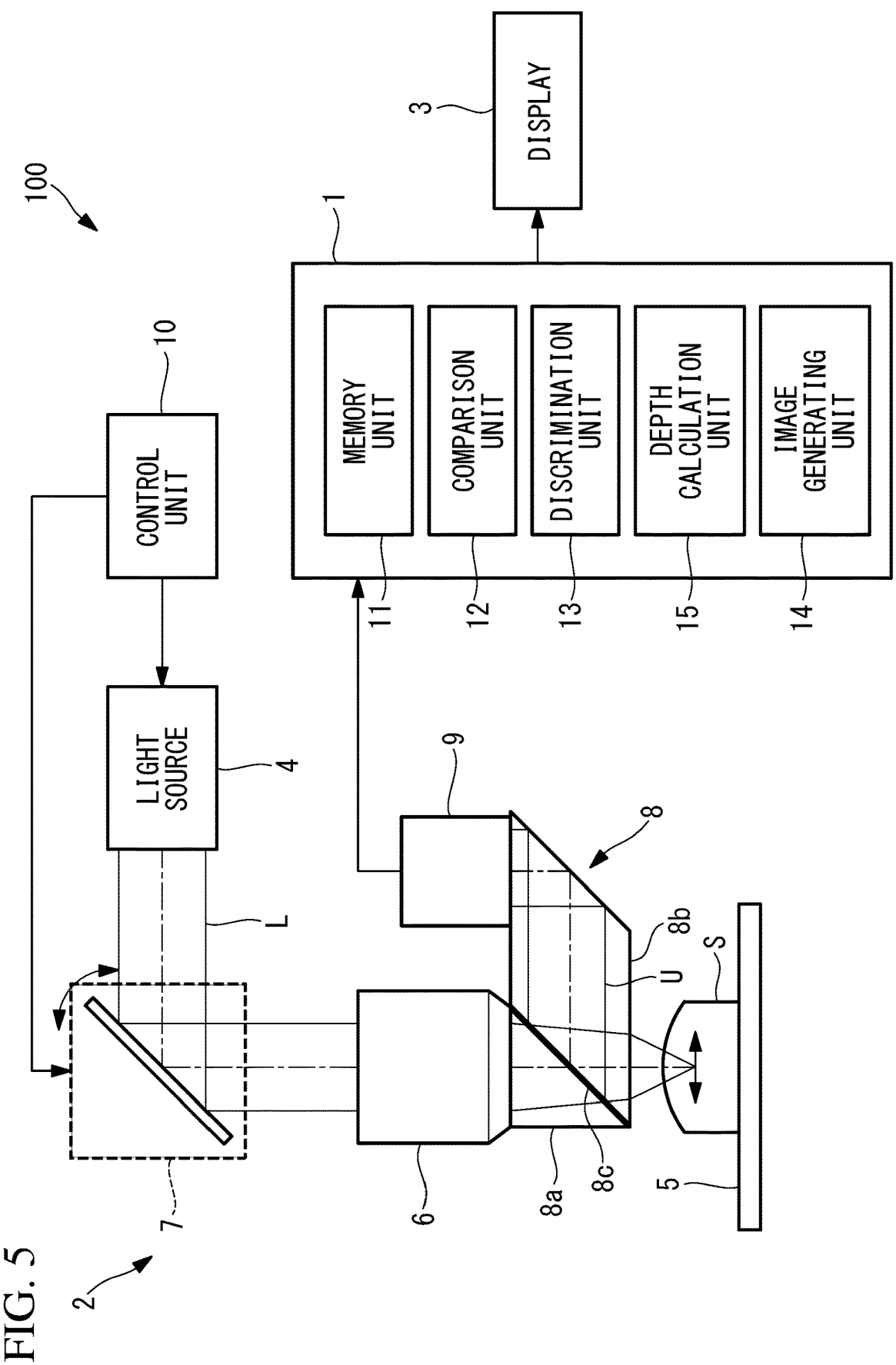

SIGNAL PROCESSING DEVICE, PHOTOACOUSTIC WAVE IMAGE-ACQUISITION DEVICE, AND SIGNAL PROCESSING METHOD

CROSS-REFERENCE TO RELATED APPLICATIONS

This is a continuation of International Application PCT/JP2017/002151, with an international filing date of Jan. 23, 2017, which is hereby incorporated by reference herein in its entirety.

TECHNICAL FIELD

The present invention relates to a signal processing device, a photoacoustic wave image-acquisition device, and a signal processing method.

BACKGROUND ART

There are known photoacoustic wave microscopes in which photoacoustic waves as detection signals are applied to imaging (refer to, for example, Japanese Translation of PCT International Application, Publication No. 2011-519281). A photoacoustic wave is a type of ultrasound that is generated in the process of thermal elasticity when a substance is irradiated with light of an absorption wavelength region. Photoacoustic wave microscopes are attracting attention as means for imaging absorption properties.

Japanese Translation of PCT International Application, Publication No. 2011-519281 proposes imaging of blood vessels with a photoacoustic wave microscope. More specifically, the photoacoustic wave microscope focuses, onto a specimen, pulsed light having an absorption wavelength region of hemoglobin, scans a spot of the pulsed light in the specimen, detects, with a transducer etc., a photoacoustic wave generated at each position, and generates an image on the basis of the intensity (amplitude) of the photoacoustic wave.

SUMMARY OF INVENTION

A first aspect of the present invention is a signal processing device that processes data of a detected ultrasound waveform representing a temporal change in intensity of ultrasound generated at a measurement position in a specimen, said signal processing device including: a comparison unit that compares a predetermined standard ultrasound waveform and the detected ultrasound waveform at the measurement position and that calculates a degree of similarity between the predetermined standard ultrasound waveform and the detected ultrasound waveform; and a discrimination unit that discriminates whether or not the measurement position corresponds to a predetermined examination subject on the basis of the degree of similarity calculated by said comparison unit.

In the above-described first aspect, the specimen may include a plurality of different examination subjects, and the discrimination unit may discriminate the plurality of different examination subjects.

In the above-described first aspect, the predetermined standard ultrasound waveform may be a detected ultrasound waveform at a standard position selected from among a plurality of the measurement positions or may be an ultrasound waveform pre-measured before acquisition of the data.

In the above-described first aspect, the comparison unit may calculate a correlation coefficient between the standard ultrasound waveform and the detected ultrasound waveform while relatively shifting the standard ultrasound waveform and the detected ultrasound waveform in a time axis direction and may calculate the maximum value of the calculated correlation coefficient as the degree of similarity.

In the above-described first aspect, the comparison unit may calculate a time difference between the standard ultrasound waveform and the detected ultrasound waveform when the correlation coefficient becomes maximum, and the signal processing device may include a depth calculation unit that calculates a depth of the measurement position on the basis of the time difference calculated by the comparison unit and a velocity of the ultrasound.

The above-described first aspect may include an image generating unit that generates an ultrasound image on the basis of the intensity of the detected ultrasound waveform, wherein said image generating unit may correct contrast of the ultrasound image on the basis of the depth calculated by the depth calculation unit.

In the above-described first aspect, the comparison unit may calculate a frequency component included in the standard ultrasound waveform, may calculate a frequency component included in the detected ultrasound waveform, and may compare the calculated frequency component of the standard ultrasound waveform with the calculated frequency component of the detected ultrasound waveform, thereby calculating the degree of similarity.

A second aspect of the present invention is a photoacoustic wave image-acquisition device including: a light source that irradiates a specimen with excitation light; a photoacoustic wave detection unit that detects ultrasound generated at a measurement position in the specimen as a result of the specimen being irradiated with the excitation light and that acquires a waveform of the detected ultrasound; and one of the above-described signal processing devices that process data of the detected ultrasound waveform acquired by said photoacoustic wave detection unit.

A third aspect of the present invention is a signal processing method for processing data of a detected ultrasound waveform representing a temporal change in intensity of ultrasound that is generated at a measurement position in a specimen as a result of the specimen being irradiated with excitation light, said method including: comparing a predetermined standard ultrasound waveform with the detected ultrasound waveform at the measurement position and calculating a degree of similarity between the predetermined standard ultrasound waveform and the detected ultrasound waveform; and discriminating whether or not the measurement position corresponds to a predetermined examination subject on the basis of the calculated degree of similarity.

BRIEF DESCRIPTION OF DRAWINGS

FIG. 5 is an overall configuration diagram of a modification of the signal processing device and the photoacoustic wave image-acquisition device in FIG. 1.

DESCRIPTION OF EMBODIMENTS

First Embodiment

A signal processing device and a photoacoustic wave image-acquisition device according to a first embodiment of the present invention will now be described with reference to FIGS. 1 to 6.

Figure 1:
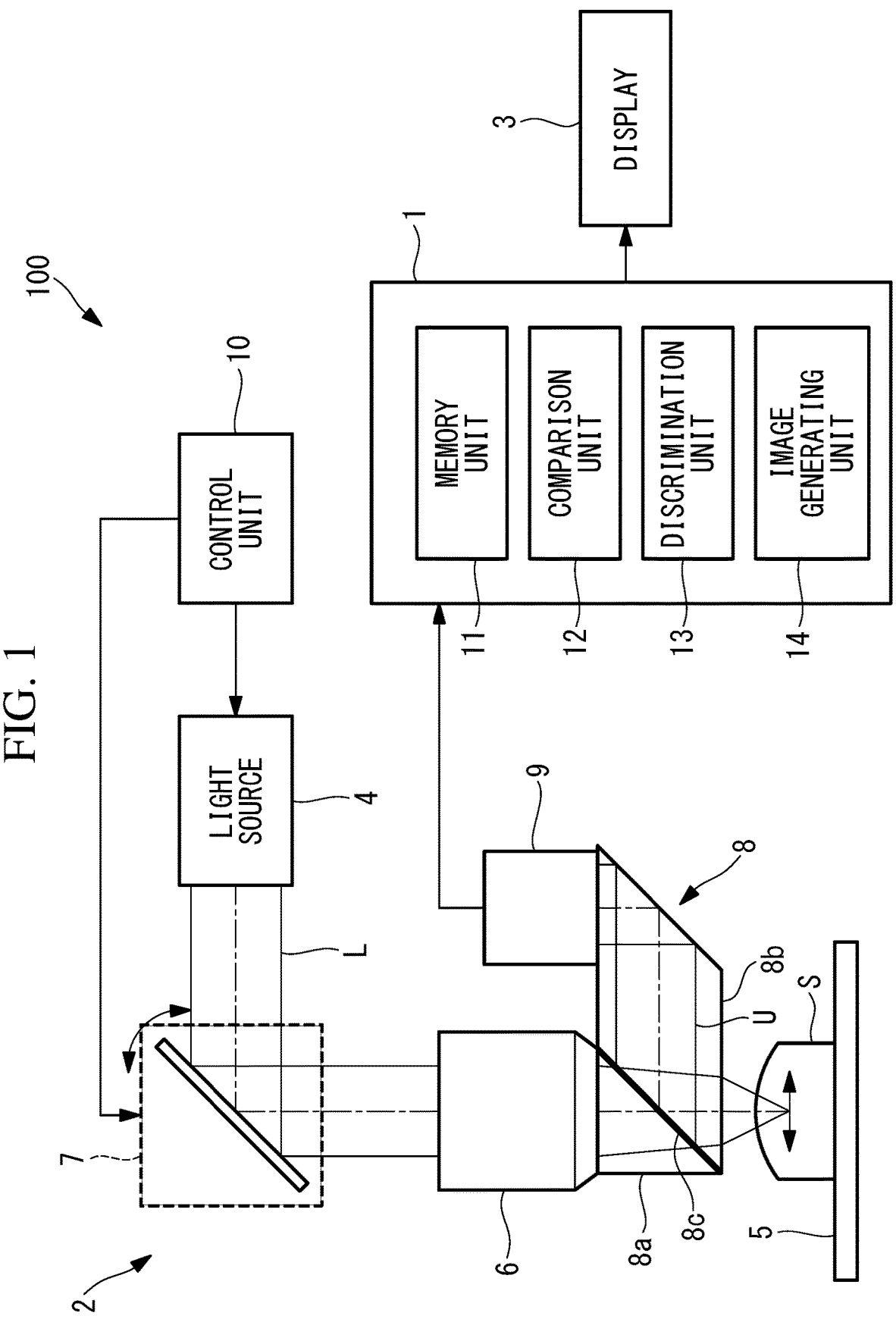
FIG. 1 is an overall configuration diagram of a signal processing device and a photoacoustic wave image-acquisition device according to a first embodiment of the present invention.

As shown in FIG. 1, a photoacoustic wave image-acquisition device 100 according to this embodiment includes: a photoacoustic wave microscope 2 that irradiates a specimen S with excitation light L and that detects a photoacoustic wave (ultrasound) U generated in the specimen S; and a signal processing device 1 that processes data of the photoacoustic wave U detected by the photoacoustic wave microscope 2 and that generates a two-dimensional image of the specimen S. Reference sign 3 denotes a display that is connected to the signal processing device 1 and that displays the image generated by the signal processing device 1.

The photoacoustic wave microscope 2 includes: a light source 4 for emitting excitation light L; a stage 5 on which the specimen S is placed; an objective lens 6 for irradiating the specimen S on the stage 5 with the excitation light L emitted from the light source 4; a light scanning part 7 for scanning the excitation light L that is to be radiated on the specimen S in a direction orthogonal to an optical axis of the objective lens 6; a photoacoustic wave reflecting part 8 that is disposed between the objective lens 6 and the specimen S and that splits off the photoacoustic wave U, which comes from the specimen S, from an optical path of the excitation light L; a photoacoustic wave detection part (photoacoustic wave detector) 9 for detecting the photoacoustic wave split off by the photoacoustic wave reflecting part 8; and a control unit 10 for controlling the light source 4 and the light scanning part 7.

The light source 4 is a pulsed light source for emitting pulsed light as the excitation light L. The excitation light L is light having an absorption wavelength of a predetermined examination subject in the specimen S. As shown in, for example, FIG. 2A, in a case where the specimen S is a living organism and a predetermined examination subject A is a blood vessel, light having an absorption wavelength of hemoglobin is used as the excitation light L. The predetermined examination subject may be an exogenous substance, such as a fluorescent member and metal nanoparticles. If a plurality of absorbing substances are present in the specimen S, it is preferable that excitation light L having a peak wavelength characteristic of the absorption spectrum of the predetermined examination subject A be used.

The objective lens 6 converges, to a focal point, the excitation light L that has been incident thereon from the light source 4 via the light scanning part 7 and forms a spot at the focal point. As the objective lens 6, a lens having a focal length such that the spot of the excitation light L is located in the specimen S is used.

The light scanning part 7 has, for example, two galvanometer mirrors and scans the excitation light L in two axis directions orthogonal to the optical axis of the objective lens 6 so that the spot of the excitation light L in the specimen S is scanned two-dimensionally.

Note that the configuration of the light scanning part 7 is not limited to that described above but may be another configuration as long as the relative position between the spot of the excitation light L and the specimen S can be changed in a direction orthogonal to the optical axis of the objective lens 6. For example, a light scanning part for moving the specimen S or the stage 5 in a direction orthogonal to the optical axis of the objective lens 6 may be employed.

The photoacoustic wave reflecting part 8 includes two prisms 8a and 8b that are each disposed in the optical path of the excitation light L and that are bonded to each other with a photoacoustic wave reflecting member 8c interposed therebetween. The photoacoustic wave reflecting member 8c is formed of a member, such as silicone oil or air, that is transparent to the excitation light L and that has a different acoustic impedance from the prism 8b on the specimen S side. The photoacoustic wave U generated at the spot of the excitation light L in the specimen S is incident on the prism 8b, is reflected in a direction different from the optical path of the excitation light L at a boundary surface between the prism 8b and the photoacoustic wave reflecting member 8c, and is incident on the photoacoustic wave detection part 9.

It is preferable that the space between the specimen S and the prism 8b and the space between the prism 8b and the photoacoustic wave detection part 9 be filled with a photoacoustic wave transmitting medium, such as water or glass, through which the photoacoustic wave U easily passes. A photoacoustic wave lens (not shown in the figure) may be disposed on the specimen S side of the prism 8b.

The photoacoustic wave detection part 9 includes, for example, a transducer and detects a photoacoustic wave emitted from the specimen S. FIGS. 3A, 3B, and 3C show examples of temporal waveforms of the intensities (amplitudes) of photoacoustic waves U at positions SP, CP1, and CP2, respectively, in FIG. 2A. As shown in FIGS. 3A to 3C, the intensities of the photoacoustic waves U excited by pulsed excitation light L change over time. The photoacoustic wave detection part 9 measures a detected ultrasound waveform, which is a waveform of a change in the intensity of the photoacoustic wave U with time, and outputs, to the signal processing device 1, the detected ultrasound waveform that has been measured.

The control unit 10 controls the timing at which the light source 4 emits light and controls the light scanning part 7 in synchronization with the timing at which the light source 4 emits light, thereby the irradiation position of the excitation light L is two dimensionally moved in a predetermined image acquisition area of an image. By doing so, detected ultrasound waveforms at many measurement positions corresponding to respective pixels of the image are sequentially measured by the photoacoustic wave detection part 9.

The signal processing device 1 includes: a memory unit 11 for storing data of detected ultrasound waveforms received from the photoacoustic wave detection part 9; a comparison unit 12 for calculating the degree of similarity between each of the detected ultrasound waveforms and a predetermined standard ultrasound waveform stored in the memory unit 11; a discrimination unit 13 for discriminating whether or not each of the measurement positions corresponds to the predetermined examination subject A on the basis of the degree of similarity; and an image generating unit 14 for generating an image of the specimen S on the basis of discrimination results from the discrimination unit 13.

The memory unit 11 stores each of the detected ultrasound waveforms so as to associate it with the measurement position thereof (two-dimensional coordinates in a plane orthogonal to the optical axis of the objective lens 6).

In addition, the memory unit 11 stores the predetermined standard ultrasound waveform. The predetermined standard ultrasound waveform is an ultrasound waveform that has been measured by the photoacoustic wave detection part 9 as a result of the predetermined examination subject being irradiated with the excitation light L. As such a predetermined standard ultrasound waveform, a detected ultrasound waveform at the standard position SP, selected from among all measurement positions, in the predetermined examination subject A is used. The standard position SP is specified by an examiner using a pointing device, such as a mouse. Alternatively, the standard position SP may be automatically set to a measurement position at which a detected ultrasound waveform with high intensity is detected.

The comparison unit 12 reads the standard ultrasound waveform and the detected ultrasound waveforms from the memory unit 11 and calculates, as the degree of similarity, a correlation coefficient between the standard ultrasound waveform and each of all detected ultrasound waveforms including the standard ultrasound waveform. Note that because the standard position SP has been selected from within a measurement area, there is barely a difference in acquisition time between the standard ultrasound waveform and each of the detected ultrasound waveforms. Therefore, a correlation coefficient that is not influenced by a temporal change of the specimen S or differences among individual specimens S, if any, can be calculated, resulting in achieving a degree of similarity with higher reliability.

At this time, the comparison unit 12 calculates a plurality of correlation coefficients by repeating the calculation of the correlation coefficient while relatively shifting a detected ultrasound waveform and the standard ultrasound waveform in the time axis direction and determines, as the degree of similarity, the maximum correlation coefficient from among the plurality of correlation coefficients.

Figure 3A:
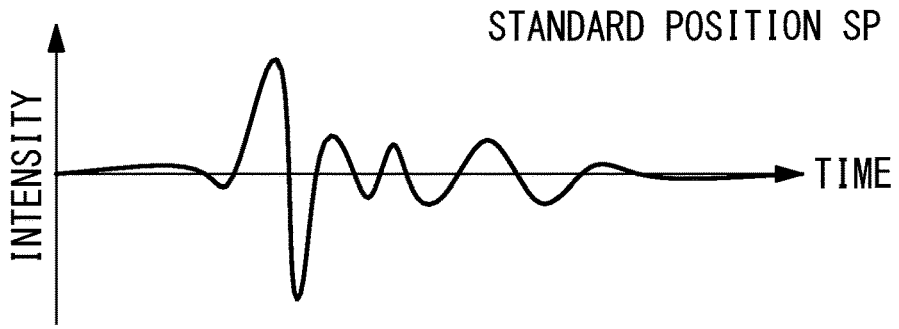
FIG. 3A is a diagram depicting one example of a standard ultrasound waveform at a standard position SP in FIG. 2A.
Figure 3B:
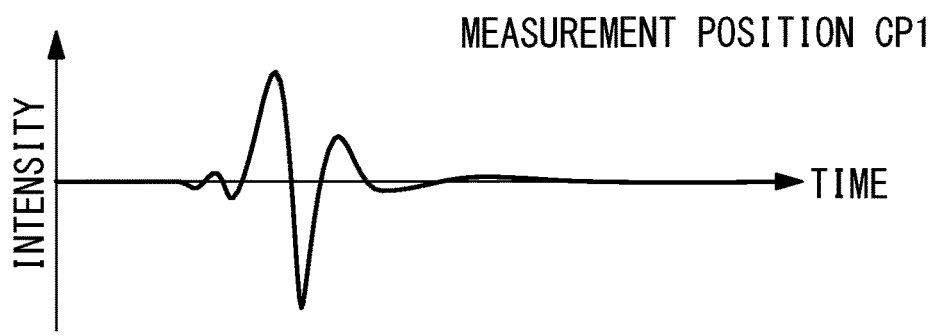
FIG. 3B is a diagram depicting one example of a detected ultrasound waveform at a measurement position CP1 in FIG. 2A.
Figure 4A:
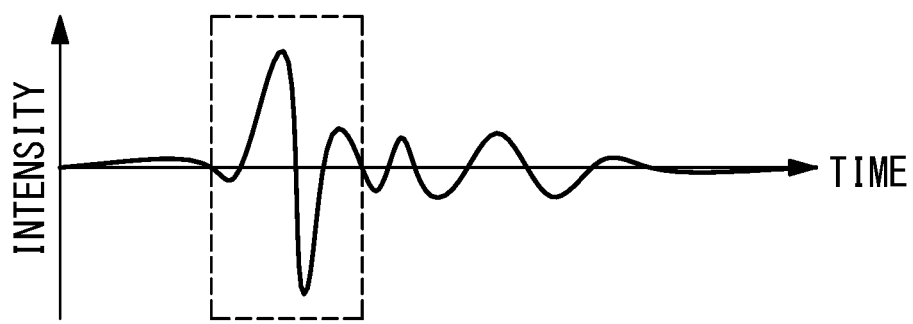
FIG. 4A is a diagram illustrating a waveform $WF_{SP}$ extracted from the standard ultrasound waveform in FIG. 2A for the calculation of a correlation coefficient.

A method for calculating a correlation coefficient will now be described by way of an example of the standard ultrasound waveform in FIG. 3A and the detected ultrasound waveform in FIG. 3B. First of all, a partial waveform $WF_{SP}$, as shown in FIG. 4A, used for calculation of a correlation coefficient is extracted from the standard ultrasound waveform. A time period from which the waveform $WF_{SP}$ is extracted (the time period enclosed by the broken line in FIG. 4A) is set to a time period in which the absolute value of the intensity of the photoacoustic wave U exceeds a threshold value.

Next, a search scope in which the correlation coefficient is calculated is set in the detected ultrasound waveform.

Figure 4B:
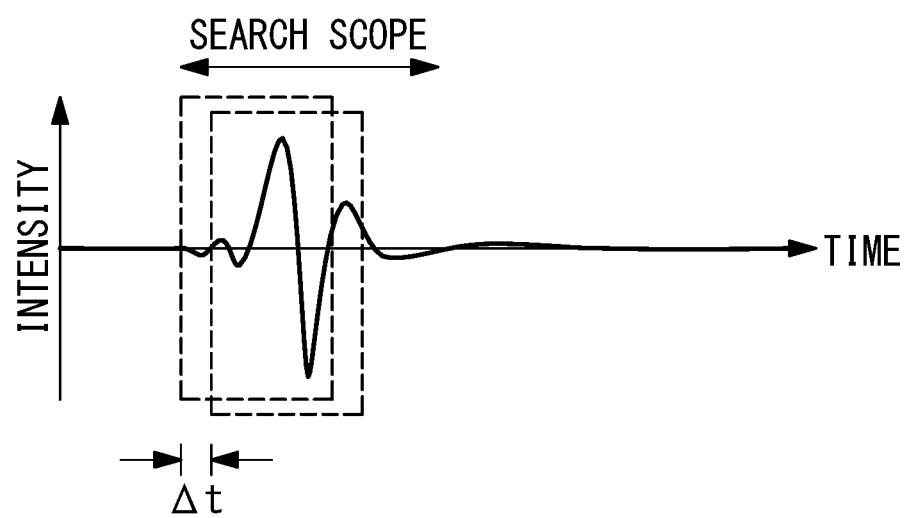
FIG. 4B is a diagram illustrating a waveform $WF_{CP1}$ extracted from the detected ultrasound waveform in FIG. 2B for the calculation of a correlation coefficient.

Next, as shown in FIG. 4B, a target time period from which a waveform used to calculate the correlation coefficient is extracted (time period enclosed by a broken line in FIG. 4B) is set in the search scope. It is preferable that the length of the target time period be equal to the length of the time period for extracting the waveform $WF_{SP}$. At this time, when the first correlation coefficient is calculated, the target time period is set to the time position at which the start time of the search scope and the start time of the target time period coincide with each other. A time position is a coordinate on a time coordinate axis and indicates a particular time period. Next, a waveform $WF_{CP1}$ in the target time period is extracted from the detected ultrasound waveform. Next, a correlation coefficient between the waveform $WF_{SP}$ and the waveform $WF_{CP1}$ is calculated. The calculated correlation coefficient is saved in a working memory (not shown in the figure).

Next, the time position of the target time period is shifted backward by a unit time $\Delta t$, and the waveform $WF_{CP1}$ in the shifted target time period is extracted. Next, a correlation coefficient between the waveform $WF_{SP}$ and the waveform $WF_{CP1}$ is calculated. The calculated correlation coefficient is saved in the working memory (not shown in the figure).

Subsequently, while shifting backward the time position of the target time period by the unit time $\Delta t$, extraction of the waveform $WF_{CP1}$ in the target time period, calculation of a correlation coefficient between the extracted waveform $WF_{CP1}$ and the waveform $WF_{SP}$, and saving of the correlation coefficient are repeated until the end time of the target time period reaches the end time of the search scope.

The comparison unit 12 determines, as the degree of similarity, the maximum correlation coefficient from among the correlation coefficients stored in the working memory.

The spot of the excitation light L spreads in the depth direction (optical-axis direction of the objective lens 6) about the focal point of the objective lens 6, and thus the depth of an absorbing substance that generates a photoacoustic wave U, i.e., the depth of the measurement position, may vary in the spot. Therefore, the detected ultrasound waveform can shift in the time axis direction relative to the standard ultrasound waveform according to the relative depths of the measurement positions CP1 and CP2 with respect to the depth of the standard position SP. As described above, the maximum value of the correlation coefficients calculated at a plurality of time positions is a correlation coefficient between the standard ultrasound waveform and the detected ultrasound waveform in a state where there are no shifts in the time period. A degree of similarity for accurately representing the correlation between the standard ultrasound waveform and the detected ultrasound waveform can be obtained by determining, as the degree of similarity, the maximum correlation coefficient as described above.

The discrimination unit 13 determines which of a plurality of classes the degree of similarity calculated by the comparison unit 12 belongs to. More specifically, a plurality of threshold values for specifying the scopes of the respective classes are set. The discrimination unit 13 determines which class each degree of similarity belongs to by comparing the degree of similarity with the plurality of threshold values. The class of each degree of similarity is stored in the memory unit 11 in such a manner as to be associated with the detected ultrasound waveform and measurement position thereof. By doing so, data in which the detected ultrasound waveform, the measurement position, and the class are associated with one another is generated in the memory unit 11.

The shape of a detected ultrasound waveform depends on the substance that is present at the measurement positions CP1 and CP2 of this detected ultrasound waveform. In other words, at a measurement position where the same substance as the substance at the standard position SP is present, a detected ultrasound waveform having a shape the same as or similar to the shape of the standard ultrasound waveform is acquired, leading to a high degree of similarity. On the other hand, at a measurement position where the same substance as the substance at the standard position SP is not present, a detected ultrasound waveform having a different shape from the shape of the standard ultrasound waveform is acquired, resulting in a low degree of similarity. Therefore, it can be discriminated on the basis of the class of the degree of similarity whether or not each of the measurement positions CP1 and CP2 corresponds to the predetermined examination subject A.

Figure 2A:
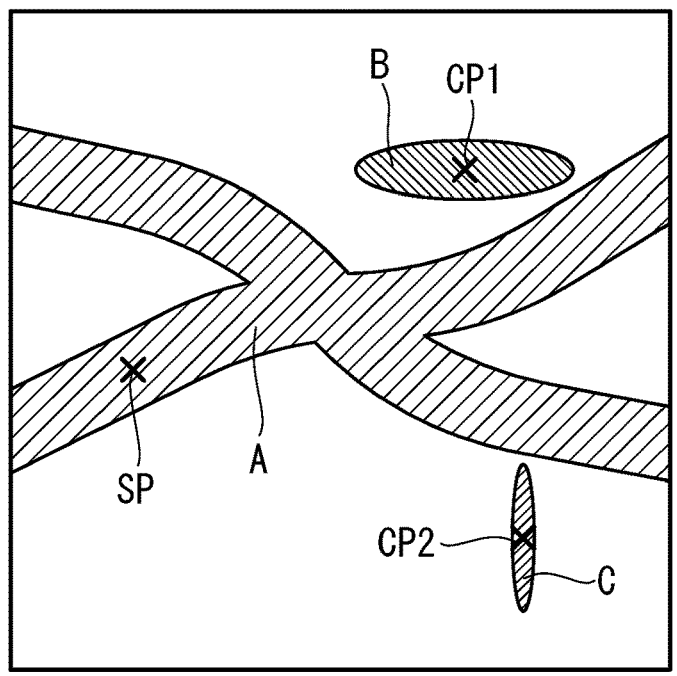
FIG. 2A is a diagram depicting one example of a specimen.
Figure 3C:
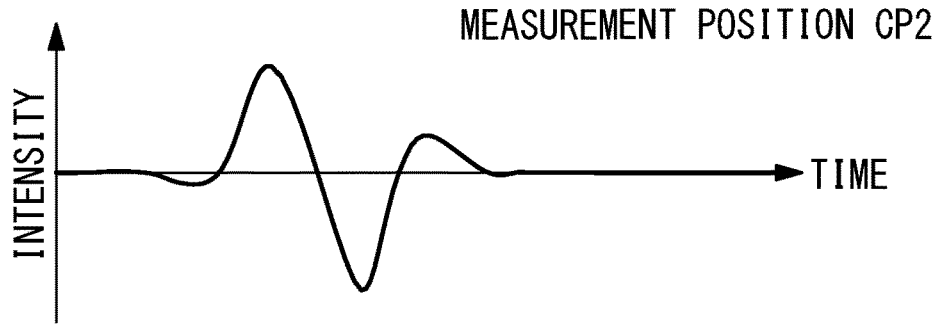
FIG. 3C is a diagram depicting one example of a detected ultrasound waveform at a measurement position CP2 in FIG. 2A.

Furthermore, as shown in FIG. 2A, if a plurality of different examination subjects A, B, and C are included in the specimen S, the plurality of different examination subjects A, B, and C can be discriminated on the basis of the degree of similarity and the class of the degree of similarity.

Figure 2B:
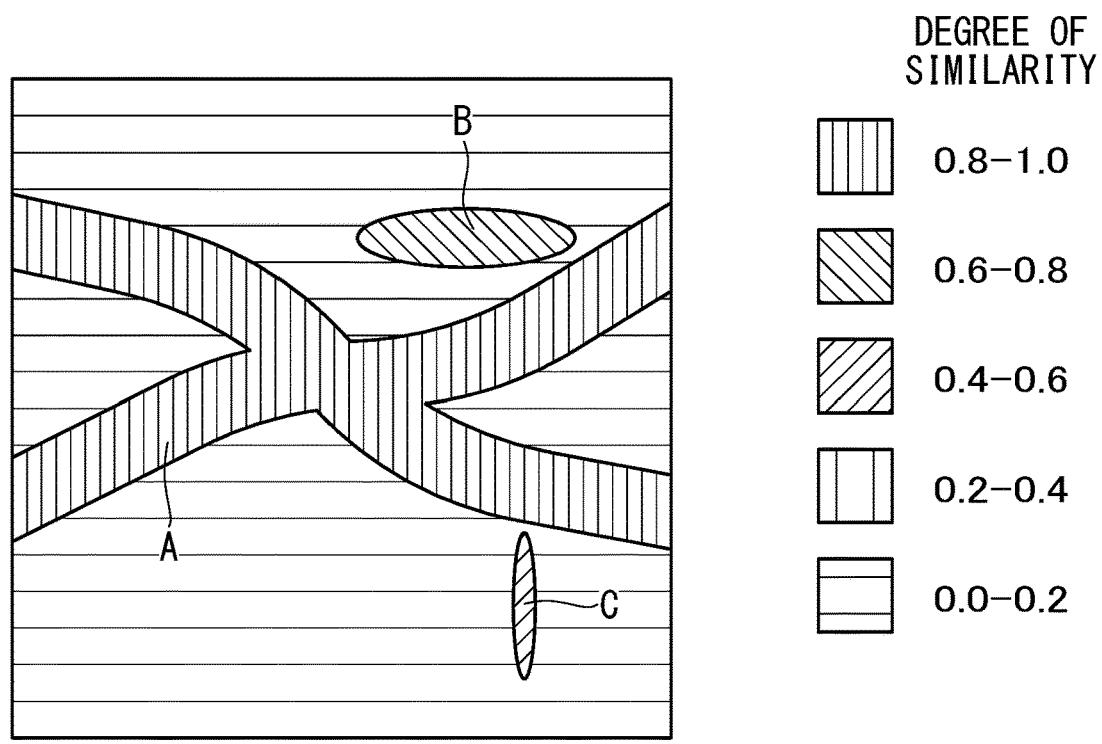
FIG. 2B is a diagram depicting one example of a degree-of-similarity map generated from the specimen in FIG. 2A.

It is assumed to be known as a precondition for image acquisition that examination subjects that generate photoacoustic waves are of three types: for example, a blood vessel, a fluorescent member, and metal nanoparticles. It is also assumed to be known that an examination subject that generates the standard ultrasound waveform is a blood vessel, the correlation coefficient between ultrasound waveforms of the blood vessel and the fluorescent member is 0.6 to 0.8, and the correlation coefficient between ultrasound waveforms of the blood vessel and the metal nanoparticle is 0.4 to 0.6. In this case, in an image acquisition result as shown in FIG. 2B, the portion having a correlation coefficient of 0.8 to 1.0 (examination subject A in FIG. 2B) can be discriminated as a blood vessel, the portion having a correlation coefficient 0.6 to 0.8 (examination subject B in FIG. 2B) can be discriminated as a fluorescent member, and the portion having a correlation coefficient 0.4 to 0.6 (examination subject C in FIG. 2B) can be discriminated as metal nanoparticles.

The image generating unit 14 stores a correspondence relationship between classes and colors. Colors are set so as to differ from one another among classes. The image generating unit 14 reads out measurement positions and classes from the memory unit 11 and assigns a color according to the corresponding class to the pixel corresponding to each of the measurement positions. By doing so, as shown in FIG. 2B, a degree-of-similarity map that is divided into colors by the classes corresponding to the degrees of similarity between the detected ultrasound waveforms and the standard ultrasound waveform is generated as an image. In FIG. 2B, the degrees of similarity are grouped into five classes on the basis of four threshold values (0.2, 0.4, 0.6, and 0.8). Differences in hatching orientation and pitch represent color differences. The generated degree-of-similarity map is output from the signal processing device 1 to the display 3 and is displayed on the display 3.

Next, the operation of the photoacoustic wave image-acquisition device 100 with the above-described structure will be described.

The pulsed excitation light L emitted from the light source 4 is incident on the objective lens 6 via the light scanning part 7, is radiated from the objective lens 6 onto the specimen S via the prism 8a, the photoacoustic wave reflecting member 8c, and the prism 8b, and forms a spot at the focal point in the specimen S. At the spot, a substance that exhibits absorption at a wavelength of the excitation light L is excited and generates a photoacoustic wave U.

Of the generated photoacoustic wave U, the photoacoustic wave U that returns in the optical path of the excitation light L is incident on the prism 8b, is reflected at the photoacoustic wave reflecting member 8c, and is detected by the photoacoustic wave detection part 9. By doing so, a detected ultrasound waveform at one measurement position is acquired. The acquired detected ultrasound waveform is transmitted from the photoacoustic wave detection part 9 to the memory unit 11 in the signal processing device 1 and is stored in the memory unit 11 in such a manner as to be associated with the measurement position.

Next, the control unit 10 controls the light scanning part 7 and the light source 4 and irradiates the next measurement position with the spot of the excitation light L. In this manner, a detected ultrasound waveform at the next measurement position is acquired by the photoacoustic wave detection part 9, and the detected ultrasound waveform is stored in the memory unit 11.

Hereinafter, shifting of the spot of the excitation light L and acquisition of a detected ultrasound waveform are repeated in the same manner, thereby causing detected ultrasound waveforms at all measurement positions in the predetermined image acquisition area to be acquired and then to be stored in the memory unit 11, said measurement positions corresponding to all pixels of an image.

In the signal processing device 1, a signal processing method is performed as follows.

First of all, correlation coefficients between the standard ultrasound waveform and each of the detected ultrasound waveforms stored in the memory unit 11 are calculated in the comparison unit 12, and the maximum correlation coefficient is calculated as the degree of similarity. Next, as a result of each degree of similarity being grouped into one of a plurality of classes in the discrimination unit 13, it is discriminated whether or not each of the measurement positions corresponds to the predetermined examination subject A on the basis of the class of the degree of similarity. If the specimen S contains a plurality of examination subjects, the plurality of different examination subjects are discriminated on the basis of the class of the degree of similarity. The class of each of the measurement positions is stored in the memory unit 11.

Next, in the image generating unit 14, a degree-of-similarity map of the specimen S that is divided into colors by the classes corresponding to the degrees of similarity is generated on the basis of the measurement positions and the classes of the degrees of similarity stored in the memory unit 11. In the degree-of-similarity map, positions where the same substance as that at the standard position SP is present are indicated in the same color as that of the standard position SP, and the other positions are indicated in different colors from that of the standard position SP. Here, because the standard position SP is a position in the predetermined examination subject A, it is discriminated by color whether or not those positions correspond to the predetermined examination subject. If the predetermined examination subject A is, for example, a blood vessel, all regions corresponding to a blood vessel are indicated in the same color, and regions other than a blood vessel are indicated in other colors.

If an absorbing substance, other than the predetermined examination subject A, that generates a photoacoustic wave U due to the excitation light L is present, a photoacoustic wave U is also generated in the substance other than the examination subject A. In this case, it is difficult to discriminate, on the basis of the intensity of the photoacoustic wave U, the absorbing substances that generate photoacoustic waves U. For this reason, it is difficult to discriminate, on the basis of a luminance value of an image, whether or not the image corresponds to the predetermined examination subject A.

This embodiment affords an advantage in that it is possible to accurately determine whether or not an absorbing substance that generates a photoacoustic wave U is the same as the absorbing substance in the predetermined examination subject A on the basis of the degree of similarity between the detected ultrasound waveform at each of the measurement positions in the specimen S and the standard ultrasound waveform, thereby making it possible to accurately determine whether or not each of the measurement positions corresponds to the predetermined examination subject A. This embodiment affords another advantage in that the examiner can be presented with an image in which whether or not a measurement position corresponds to the predetermined examination subject A can be accurately discriminated by color as a result of the degrees of similarity being mapped. This embodiment affords another advantage in that if the specimen S includes a plurality of examination subjects A, B, and C, the plurality of examination subjects A, B, and C can be accurately discriminated on the basis of the degree of similarity between the detected ultrasound waveform at each of the measurement positions in the specimen S and the standard ultrasound waveform.

In this embodiment, in addition to the degree-of-similarity map, the image generating unit 14 may generate a photoacoustic wave image (ultrasound image) in which the luminance value at each pixel is a value based on the intensity (amplitude) of the detected ultrasound waveform.

In this case, the image generating unit 14 may remove noise in the photoacoustic wave image by removing, from the photoacoustic wave image, pixels of a class with a low degree of similarity in the degree-of-similarity map. Because objects other than the examination subject are selectively removed by removing pixels with a low degree of similarity in this manner, a photoacoustic wave image in which only the examination subject is extracted can be obtained.

As shown in FIG. 5, this embodiment may further include a depth calculation unit 15 for calculating the depth of each of the measurement positions.

As described above, the detected ultrasound waveform shifts in the time axis direction according to the depth of the measurement position CP1, and the relative depth of the measurement position CP1 with respect to the standard position SP can be calculated on the basis of the time difference between the waveform $WF_{CP1}$ with which the maximum correlation coefficient can be obtained and the waveform $WF_{SP}$ of the standard ultrasound waveform. More specifically, the depth calculation unit 15 calculates the difference between the time position of the time period in which the waveform $WF_{SP}$ is extracted from within the standard ultrasound waveform and the time position of the target time period of the waveform $WF_{CP1}$ in which the maximum correlation coefficient is obtained and multiplies the calculated difference by the velocity of the photoacoustic wave U, thereby calculating the relative depth of the measurement position CP1 with respect to the standard position SP.

In the configuration including the depth calculation unit 15 in FIG. 5, the image generating unit 14 may correct the contrast of the photoacoustic wave image on the basis of the depth of each of the measurement positions calculated by the depth calculation unit 15.

The intensity (amplitude) of the photoacoustic wave U changes according to the intensity of the excitation light L radiated on the absorbing substance. Therefore, the intensity of the photoacoustic wave U is maximized at the focal position of the objective lens 6 at which the intensity of the excitation light L is maximized and decreases as the distance from the focal position increases. More specifically, a correspondence relationship as shown in FIG. 6 holds between the intensity of the excitation light L and the distance from the focal position.

Figure 6:
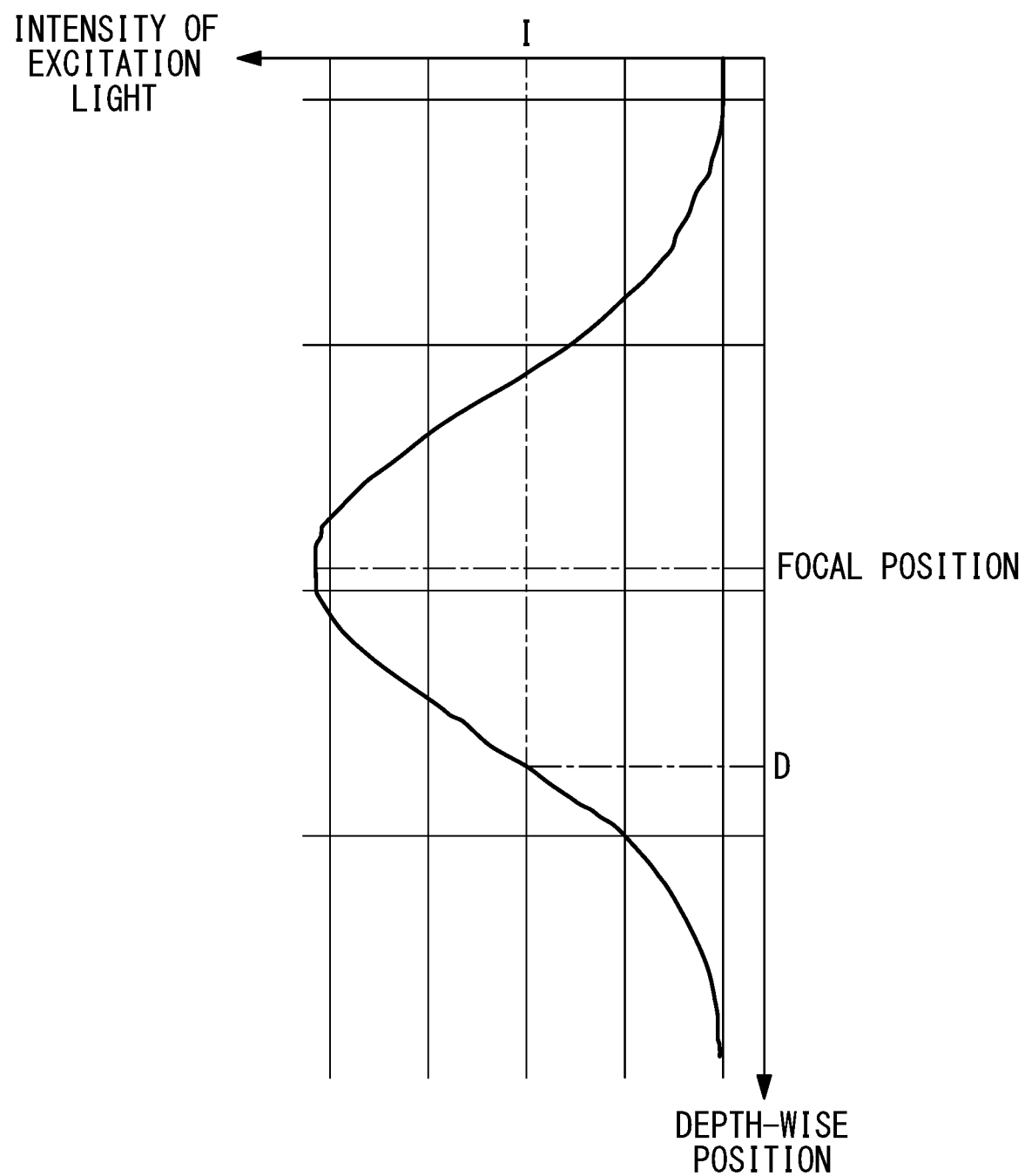
FIG. 6 is a graph showing a correspondence relationship between the intensity of excitation light and the distance from the focal position.

The image generating unit 14 stores the correspondence relationship shown in FIG. 6, calculates, from this correspondence relationship, the intensity I of the excitation light L corresponding to a depth D of each of the measurement positions, and calculates a correction coefficient by dividing the intensity of the excitation light L at the focal position by the intensity I. Next, the image generating unit 14 corrects the luminance value by multiplying the luminance value of each pixel by the correction coefficient and generates a photoacoustic wave image using the corrected luminance value. This corrects luminance value variations resulting from variations in the depth of the measurement position, thereby making it possible to correct the contrast of the photoacoustic wave image so as to achieve contrast based on differences in the intensity of the photoacoustic wave U as if the absorbing substance were irradiated with the excitation light L with the same intensity.

Second Embodiment

Figure 7A:
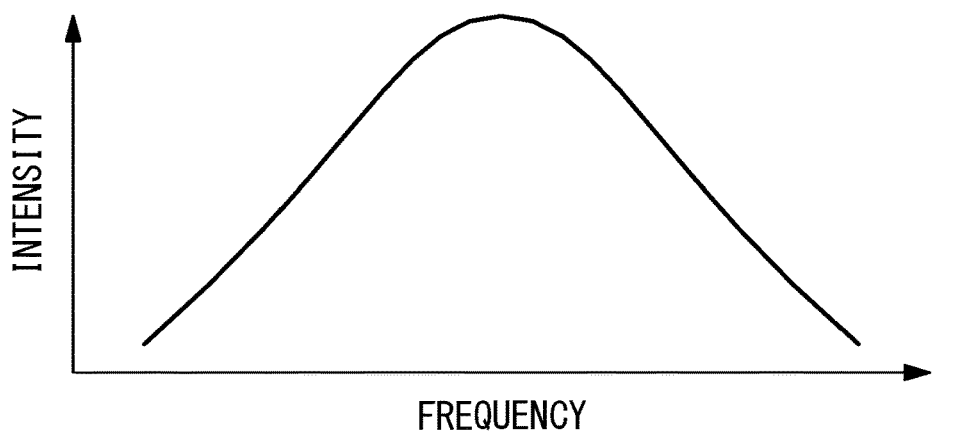
FIG. 7A is a diagram depicting one example of a frequency spectrum calculated by a comparison unit from a standard ultrasound waveform in a signal processing device and a photoacoustic wave image-acquisition device according to a second embodiment of the present invention.
Figure 7B:
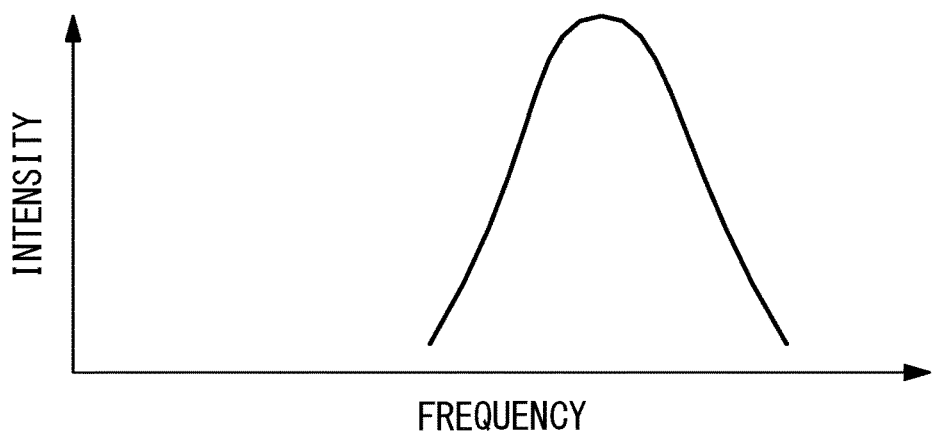
FIG. 7B is a diagram depicting one example of a frequency spectrum calculated by the comparison unit from a detected ultrasound waveform in the signal processing device and the photoacoustic wave image-acquisition device according to the second embodiment of the present invention.
Figure 7C:
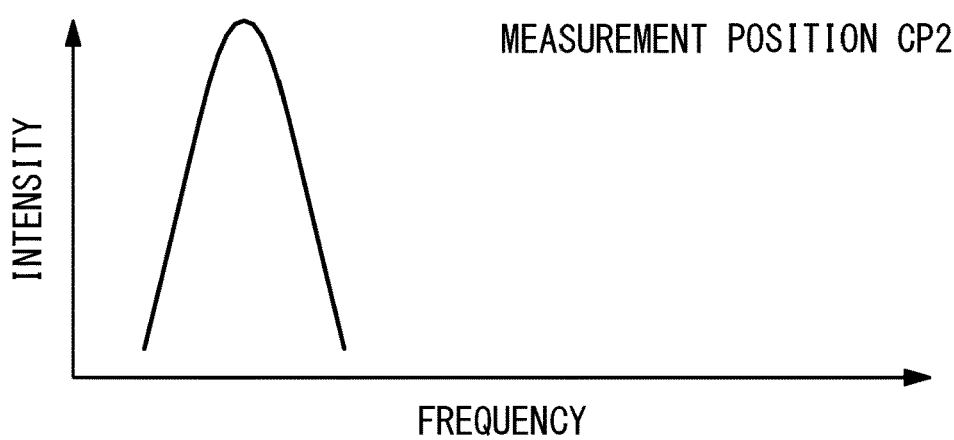
FIG. 7C is a diagram depicting one example of a frequency spectrum calculated by the comparison unit from another detected ultrasound waveform in the signal processing device and the photoacoustic wave image-acquisition device according to the second embodiment of the present invention.

Next, a signal processing device and a photoacoustic wave image-acquisition device according to a second embodiment of the present invention will be described with reference to FIGS. 7A to 7C.

In this embodiment, configurations different from those in the first embodiment will be described, configurations common to those in the first embodiment will be denoted by the same reference signs, and a description thereof will be omitted.

Similarly to the photoacoustic wave image-acquisition device 100 according to the first embodiment, the photoacoustic wave image-acquisition device according to this embodiment includes the signal processing device 1 and the photoacoustic wave microscope 2. However, a method for calculating the degree of similarity using the comparison unit 12 differs from that in the first embodiment.

In this embodiment, the comparison unit 12 calculates frequency components included in a standard ultrasound waveform by subjecting the standard ultrasound waveform to frequency conversion. In addition, the comparison unit 12 subjects each of all the detected ultrasound waveforms, including the standard ultrasound waveform, to frequency conversion, thereby calculating frequency components included in each of the detected ultrasound waveforms. FIG. 7A shows one example of a frequency spectrum of the standard ultrasound waveform at the standard position SP, and FIGS. 7B and 7C show examples of frequency spectra of the detected ultrasound waveforms at the measurement positions CP1 and CP2, respectively.

Next, the comparison unit 12 calculates the degree of similarity between the standard ultrasound waveform and each of the detected ultrasound waveforms on the basis of comparison between frequency components of the standard ultrasound waveform and frequency components of the detected ultrasound waveform.

Comparison between frequency components is performed, for example, by calculating the correlation coefficient between the frequency spectrum waveform of the standard ultrasound waveform and the frequency spectrum waveform of the detected ultrasound waveform. In this case, the calculated correlation coefficient is used as the degree of similarity.

Comparison of frequency components between the standard ultrasound waveform and the detected ultrasound waveform may be performed across the entire frequency band or may be performed in a partial band only. Comparison between frequency spectra may be performed, for example, for high-frequency components only, low-frequency components only, or particular frequency components only. Alternatively, comparison between peak frequencies may be performed, or frequency bands having an intensity equal to or higher than a threshold value may be compared. Combinations of any of the above-described examples may be employed.

As described above, according to this embodiment, in a case where frequency components are used to calculate the degree of similarity, various standards can be set as a standard for the calculation of the degree of similarity between the standard ultrasound waveform and a detected ultrasound waveform. This affords an advantage in that it can be more accurately discriminated whether or not each of the measurement positions corresponds to the predetermined examination subject A.

In addition, in a case where correlation calculation is used for comparison between frequency components, one calculation is sufficient as the required number of times correlation calculation is to be performed. Therefore, the second embodiment affords an advantage in that the amount of calculation and the calculation time can be reduced, compared with the first embodiment, which requires a large number of correlation calculations. In particular, when the depth-wise distribution of the predetermined examination subject A is wide, the method in the first embodiment requires a large number of calculations of the correlation coefficient between the standard ultrasound waveform and a detected ultrasound waveform, and hence, the method for calculating the degree of similarity in this embodiment is more advantageous in terms of the amount of calculation and the calculation time.

Also in this embodiment, the image generating unit 14 may generate a photoacoustic wave image, may discriminate a plurality of different examination subjects on the basis of a degree-of-similarity map, and may remove noise of the photoacoustic wave image.

In the above-described first and second embodiments, an ultrasound waveform measured at any standard position SP in the image acquisition area of an image is used as the standard ultrasound waveform. Instead of this, an ultrasound waveform pre-measured before image acquisition may be used.

For example, an ultrasound waveform generated by a blood vessel as a result of the blood vessel being irradiated with the excitation light L is pre-acquired before image acquisition, and the acquired ultrasound waveform is stored in the memory unit 11 as the standard ultrasound waveform. This eliminates the need to process the examiner's specification of a standard position SP and automatic selection of a standard position SP from among many measurement positions.

Figure 8:
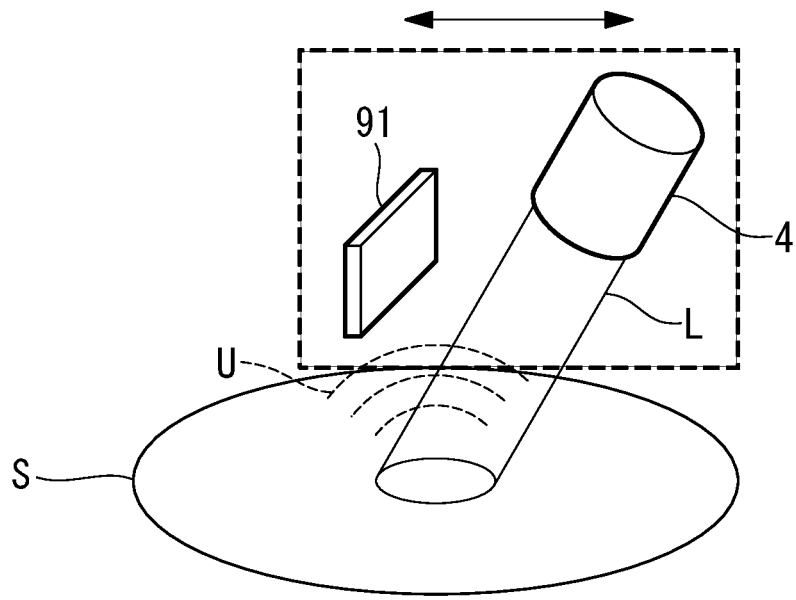
FIG. 8 is a diagram depicting a modification of the photoacoustic wave detection unit.

In this embodiment, the excitation light L focused by the objective lens 6 is scanned two-dimensionally in order to detect a photoacoustic wave U from many measurement positions in a two-dimensional plane. Instead of this, a photoacoustic wave detection part 91 may be shifted relative to the specimen S, as shown in FIG. 8. The photoacoustic wave detection part 91 includes a transducer array in which a plurality of transducers are arranged one-dimensionally and is scanned in a direction intersecting the transducer array. The excitation light L is also scanned together with movement of the photoacoustic wave detection part 91. Instead of scanning the excitation light L, the entire image acquisition area may be irradiated with the excitation light L.

Figure 9:
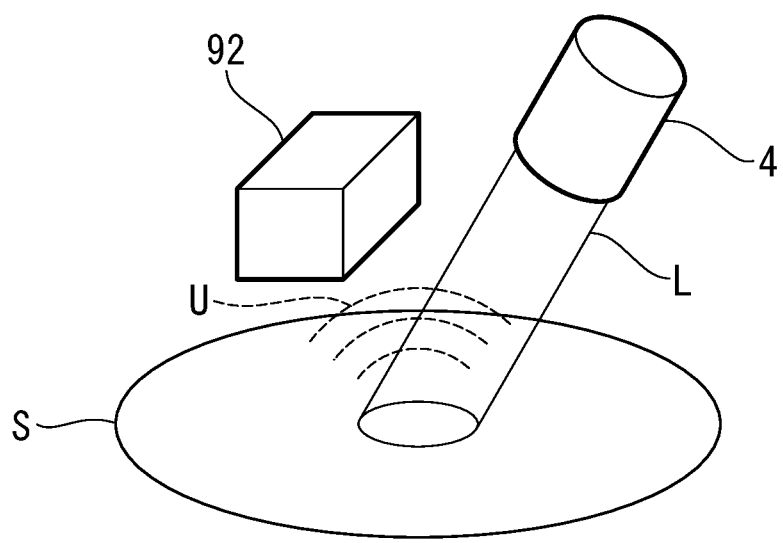
FIG. 9 is a diagram depicting another modification of the photoacoustic wave detection unit.

Alternatively, a photoacoustic wave detection part 92 including a transducer array in which a plurality of transducers are arranged two-dimensionally may be employed, as shown in FIG. 9. In this case, the entire image acquisition area is irradiated with the excitation light L.

Although the above-described first and second embodiments have been described by way of an example where the specimen S is a living organism and the predetermined examination subject A is a blood vessel, the specimen S and the predetermined examination subject A are not limited to those described above. Instead of this, any examination subject in any specimen may be examined, and a specimen S including a plurality of different examination subjects may be examined.

Although a photoacoustic wave U generated as a result of irradiation of the excitation light L is detected in the above-described first and second embodiments, radiation energy for generating ultrasound in the specimen S is not limited to light. Instead of light, another type of radiation energy may be used. For example, the specimen S may be irradiated with ultrasound, a reflected wave of ultrasound from the specimen S may be detected, and a temporal waveform of the detected wave that has been reflected may be processed by the signal processing device 1.

The above-described signal processing device 1 is realized by a computer including a CPU (central processing unit); an auxiliary storage device, such as an HDD, for storing programs for causing the CPU to execute processing of the comparison unit 12, the discrimination unit 13, the image generating unit 14, and the depth calculation unit 15; and a main storage device, such as a RAM or a ROM, to which the CPU loads the programs from the auxiliary storage device to execute processing. The memory unit 11 may be realized by the main storage device or may be realized by another storage device.

As a result, the following aspect is read from the above described embodiment of the present invention.

A first aspect of the present invention is a signal processing device that processes data of a detected ultrasound waveform representing a temporal change in intensity of ultrasound generated at a measurement position in a specimen, said signal processing device including: a comparison unit that compares a predetermined standard ultrasound waveform and the detected ultrasound waveform at the measurement position and that calculates a degree of similarity between the predetermined standard ultrasound waveform and the detected ultrasound waveform; and a discrimination unit that discriminates whether or not the measurement position corresponds to a predetermined examination subject on the basis of the degree of similarity calculated by said comparison unit.

According to the first aspect of the present invention, the degree of similarity between the detected ultrasound waveform measured at the measurement position in the specimen and the predetermined standard ultrasound waveform is calculated. The detected ultrasound waveform is determined according to the substance that is present at the measurement position. More specifically, when the substance at the measurement position is the same as the substance at the position at which the standard ultrasound waveform is measured, the degree of similarity calculated by the comparison unit is high. On the other hand, when the substance at the measurement position differs from the substance at the position at which the standard ultrasound waveform is measured, the degree of similarity calculated by the comparison unit is low. Therefore, it is possible to discriminate by means of the discrimination unit whether or not the measurement position corresponds to the predetermined examination subject by using the standard ultrasound waveform measured from the examination subject.

In the above-described first aspect, the specimen may include a plurality of different examination subjects, and the discrimination unit may discriminate the plurality of different examination subjects.

The degree of similarity between the standard ultrasound waveform and the detected ultrasound waveform at each of the examination subjects is a value within a certain range, and the range differs according to the examination subject. Therefore, the plurality of examination subjects can be discriminated from one another on the basis of the difference in the degree of similarity.

In the above-described first aspect, the predetermined standard ultrasound waveform may be a detected ultrasound waveform at a standard position selected from among a plurality of the measurement positions or may be an ultrasound waveform pre-measured before acquisition of the data.

In the above-described first aspect, the comparison unit may calculate a correlation coefficient between the standard ultrasound waveform and the detected ultrasound waveform while relatively shifting the standard ultrasound waveform and the detected ultrasound waveform in a time axis direction and may calculate the maximum value of the calculated correlation coefficient as the degree of similarity.

By doing so, it is possible to calculate the degree of similarity on the basis of the entire shape of the waveform.

In the above-described first aspect, the comparison unit may calculate a time difference between the standard ultrasound waveform and the detected ultrasound waveform when the correlation coefficient becomes maximum, and the signal processing device may include a depth calculation unit that calculates a depth of the measurement position on the basis of the time difference calculated by the comparison unit and a velocity of the ultrasound.

By doing so, it is possible to acquire information about the depth of the measurement position.

The above-described first aspect may include an image generating unit that generates an ultrasound image on the basis of the intensity of the detected ultrasound waveform, wherein said image generating unit may correct contrast of the ultrasound image on the basis of the depth calculated by the depth calculation unit.

The intensity (amplitude) of each of the detected ultrasound waveforms changes according to the depth of the measurement position. By using the depth calculated by the comparison unit, it is possible to correct the contrast of the ultrasound image so that the contrast appropriately reflects the intensity of the ultrasound at the measurement position.

In the above-described first aspect, the comparison unit may calculate a frequency component included in the standard ultrasound waveform, may calculate a frequency component included in the detected ultrasound waveform, and may compare the calculated frequency component of the standard ultrasound waveform with the calculated frequency component of the detected ultrasound waveform, thereby calculating the degree of similarity.

By doing so, compared with a case where the correlation coefficient between the standard ultrasound waveform and the detected ultrasound waveform is obtained, the amount of calculation required to calculate the degree of similarity can be reduced. In addition, various standards can be defined as the calculation standard for the degree of similarity.

A second aspect of the present invention is a photoacoustic wave image-acquisition device including: a light source that irradiates a specimen with excitation light; a photoacoustic wave detection unit that detects ultrasound generated at a measurement position in the specimen as a result of the specimen being irradiated with the excitation light and that acquires a waveform of the detected ultrasound; and one of the above-described signal processing devices that process data of the detected ultrasound waveform acquired by said photoacoustic wave detection unit.

A third aspect of the present invention is a signal processing method for processing data of a detected ultrasound waveform representing a temporal change in intensity of ultrasound that is generated at a measurement position in a specimen as a result of the specimen being irradiated with excitation light, said method including: comparing a predetermined standard ultrasound waveform with the detected ultrasound waveform at the measurement position and calculating a degree of similarity between the predetermined standard ultrasound waveform and the detected ultrasound waveform; and discriminating whether or not the measurement position corresponds to a predetermined examination subject on the basis of the calculated degree of similarity.

REFERENCE SIGNS LIST

1 Signal processing device
2 Photoacoustic wave microscope
3 Display
4 Light source
5 Stage
6 Objective lens
7 Light scanning part
8 Photoacoustic wave reflecting part
9 Photoacoustic wave detection unit (photoacoustic wave detector)
10 Control unit
11 Memory unit
12 Comparison unit
13 Discrimination unit
14 Image generating unit
15 Depth calculation unit
100 Photoacoustic wave image-acquisition device
L Excitation Light
U Photoacoustic wave (ultrasound)

The invention claimed is:

1. A signal processing device configured to process data of a detected ultrasound waveform representing a temporal change in intensity of ultrasound generated at a measurement position in a specimen, said signal processing device comprising at least one processor configured to:
   compare a predetermined standard ultrasound waveform and the detected ultrasound waveform at the measurement position and calculate a degree of similarity between the predetermined standard ultrasound waveform and the detected ultrasound waveform; and
   discriminate whether or not the measurement position corresponds to a predetermined examination subject based on the calculated degree of similarity.

2. The signal processing device according to claim 1, wherein:
   the specimen includes a plurality of different examination subjects, and
   the at least one processor is further configured to discriminate the plurality of different examination subjects.

3. The signal processing device according to claim 1, wherein:
   the specimen comprises a plurality of measurement positions, and
   the predetermined standard ultrasound waveform is a detected ultrasound waveform at a standard position selected from among the plurality of the measurement positions.

4. The signal processing device according to claim 1, wherein:
   the predetermined standard ultrasound waveform is an ultrasound waveform pre-measured before acquisition of the data of the detected ultrasound waveform.

5. The signal processing device according to claim 1, wherein the at least one processor is further configured to:
   calculate a correlation coefficient between the standard ultrasound waveform and the detected ultrasound waveform while relatively shifting the standard ultrasound waveform and the detected ultrasound waveform in a time axis direction, and
   calculate the maximum value of the calculated correlation coefficient as the degree of similarity.

6. The signal processing device according to claim 5, wherein the at least one processor is further configured to:
   calculate a time difference between the standard ultrasound waveform and the detected ultrasound waveform when the correlation coefficient becomes maximum, and
   calculate a depth of the measurement position based on the calculated time difference and a velocity of the ultrasound.

7. The signal processing device according to claim 6, wherein the at least one processor is further configured to:
   generate an ultrasound image based on the intensity of the detected ultrasound waveform, and
   correct contrast of the ultrasound image based on the calculated depth of the measurement position.

8. The signal processing device according to claim 1, wherein the at least one processor is further configured to:
   calculate a frequency component included in the standard ultrasound waveform,
   calculate a frequency component included in the detected ultrasound waveform, and
   compare the calculated frequency component of the standard ultrasound waveform with the calculated frequency component of the detected ultrasound waveform, thereby calculating the degree of similarity.

9. A photoacoustic wave image-acquisition device comprising:
   a light source configured to irradiate a specimen with excitation light;
   a photoacoustic wave detector configured to detect ultrasound generated at a measurement position in the specimen as a result of the specimen being irradiated with the excitation light and that acquires a waveform of the detected ultrasound; and
   the signal processing device according to claim 1 configured to process data of the detected ultrasound waveform acquired by said photoacoustic wave detector.

10. A signal processing method for processing data of a detected ultrasound waveform representing a temporal change in intensity of ultrasound generated at a measurement position in a specimen, said method comprising:
    comparing a predetermined standard ultrasound waveform with the detected ultrasound waveform at the measurement position and calculating a degree of similarity between the predetermined standard ultrasound waveform and the detected ultrasound waveform; and
    discriminating whether or not the measurement position corresponds to a predetermined examination subject based on the calculated degree of similarity.

* * * * *